United States Patent [19]

Hirschmann et al.

[11] 3,950,348

[45] Apr. 13, 1976

[54] PROCESS FOR PREPARING E-PYRIDYL-4-METHYLOXYCARBONYLLYSINE

[75] Inventors: Ralph F. Hirschmann, Blue Bell; Daniel F. Veber, Ambler, both of Pa.

[73] Assignee: Merck & Co., Inc., Rahway, N.J.

[22] Filed: Sept. 6, 1973

[21] Appl. No.: 393,351

Related U.S. Application Data

[62] Division of Ser. No. 214,384, Dec. 30, 1971, Pat. No. 3,780,015.

[52] U.S. Cl. 260/295 R; 260/295 AM; 260/112.5 R
[51] Int. Cl.² .................................... C07D 213/55
[58] Field of Search .................. 260/295 R, 295.5 R

[56] References Cited
OTHER PUBLICATIONS

Schroder et al., The Peptides, Vol. I, p. 152, Academic Press, NY, 1965.

Neuberger et al., The Biochemical Journal, Vol. 37, pp. 515 & 516, 1943.

Patai, The Chemistry of the Amino Group, Interscience Publishers, pp. 669–699, 1968.

*Primary Examiner*—Alan L. Rotman
*Attorney, Agent, or Firm*—Henry H. Bassford, Jr.; J. Jerome Behan

[57] ABSTRACT

A process for preparing peptides containing lysine wherein the terminal amino group of lysine is protected by a pyridyl-4-methyloxycarbonyl group during formation of the peptide and removing this group with zinc in acid.

1 Claim, No Drawings

PROCESS FOR PREPARING E-PYRIDYL-4-METHYLOXYCARBONYLLYSINE

This is a division of application Ser. No. 214,384, filed Dec. 30, 1971, now U.S. Pat. No. 3,780,015, issued Dec. 18, 1973.

The present invention relates to a process for protecting amino groups during peptide synthesis. More particularly, this invention relates to a process for preparing peptides containing lysine wherein the terminal amino group is protected by a pyridyl-4-methyloxycarbonyl group during the peptide condensation reactions and is selectively removed by zinc in acid when the desired peptide product is obtained.

The synthesis of peptides, particularly heteropeptides, is a problem which has long challenged the art. Such products are useful in the synthesis of proteins. Some of them are therapeutically active. They are also useful in the study and analysis of proteins, especially in studies designed to gain insight into the mode of action of enzymes, hormones, and other proteins with important functions in the body.

The synthesis of peptides containing lysine has presented an especially difficult problem because of the presence of an additional terminal amino group which can cause side-reactions to occur. In most instances, the terminal amino group is prevented from entering into the peptide forming reaction by protecting it with a blocking group which is removed when the desired peptide is obtained. Several protecting groups are known in the art which are useful in the synthesis of peptides containing a lysine residue, but many of the known protecting groups are removed with great difficulty during the final stages of the synthesis or are unstable to some of the reagents generally employed in peptide synthesis.

A requirement of the protecting group for the terminal amino functionality of lysine in peptide synthesis is that it must be stable to the acidic reaction conditions generally employed in removing blocking groups, such as t-butyloxycarbonyl, from other portions of the synthesized peptide. The t-butyloxycarbonyl group may be removed under acidic conditions, for example, by treatment in trifluoroacetic acid or treatment with hydrogen chloride in anhydrous or aqueous medium. An effective protecting group for the terminal amino group of lysine should not only be stable under these acidic reaction conditions but also should be completely removed without affecting other portions of the peptide. Commonly applied blocking groups for the terminal amino functionality of lysine include benzyloxycarbonyl, trifluoroacetyl, and p-toluenesulfonyl. The benzyloxycarbonyl blocking group is not completely stable under the conditions used to remove the t-butyloxycarbonyl blocking group, and as a result, a partial loss of the terminal benzyloxycarbonyl group occurs whenever one attempts to selectively remove a t-butyloxycarbonyl blocking group in a peptide synthesis. Removal of the benzyloxycarbonyl protecting group from lysine containing peptide can be accomplished by hydrogenation in a heterogeneous system with a Noble metal catalyst. This procedure is satisfactory for small peptides, however, large peptides have a highly convoluted or folded "tertiary" structure such that the benzyloxycarbonyl group to be removed is often inaccessible to the catalyst. Moreover, removal of the benzyloxycarbonyl groups by catalytic hydrogenation becomes unsatisfactory not only when the molecule becomes too large, but in the case of sulfur containing peptides, such as peptides containing methionine or cysteine, the procedure fails even with relatively small molecules.

The trifluoroacetyl blocking group can also be employed to protect the terminal amino functionality of lysine. Removal of this blocking group is accomplished under weakly basic conditions, for example in aqueous piperidine. The disadvantage of this blocking group is that many peptide condensation reactions are run in weakly basic media, and, as a result, a loss of the trifluoroacetyl blocking group occurs during peptide synthesis leading to undesirable side reactions.

The terminal functionality of lysine has also been protected by the p-toluenesulfonyl blocking group. Although this group is stable to the acidic conditions required for the removal of the t-butyloxycarbonyl and benzyloxycarbonyl blocking groups, eventual cleavage of the p-toluenesulfonyl group is achieved only through the use of sodium in liquid ammonia; these conditions lead to unwanted side reactions with many pepties.

The pyridyl-3-methyloxycarbonyl blocking group has been employed to protect the terminal amino group of lysine. This blocking group can be removed from peptides by catalytic hydrogenation or by sodium in liquid ammonia. Removal of this protecting group by catalytic hydrogenation is satisfactory for small peptides, however, this method is not suitable for large peptides or with sulfur containing peptides. The disadvantage of using sodium in liquid ammonia, as noted above, is that undesirable side reactions accompany removal of the pyridyl-3-methyloxycarbonyl blocking group.

The pyridyl-4-methyloxycarbonyl blocking group for the terminal amino group of lysine used according to the process of the present invention has distinct advantages over the above-mentioned blocking groups. The blocking group is stable under acidic or basic conditions from pH 0–12, for example it is possible to remove even the benzyloxycarbonyl blocking group selectively in the presence of pyridyl-4-methyloxycarbonyl as for example with anhydrous hydrogen fluoride. The blocking group is also stable in aqueous or anhydrous hydrochloric acid at room temperature. In addition to the stability of the pyridyl-4-methyloxycarbonyl blocking group to the reaction conditions employed in peptide synthesis, this group can, nevertheless, be completely removed under reductive conditions, for example by zinc in the presence of acid, without effecting other portions of the peptide molecule.

According to the process of this invention, the pyridyl-4-methyloxycarbonyl blocking group is introduced into the terminal amino group of lysine by reacting a lysine heavy metal complex with pyridyl-4-methylsuccinimide carbonate.

Pyridyl-4-methylsuccinimide carbonate is prepared by reacting succinimidochloroformate, prepared according to procedures known in the art, with 4-pyridylcarbinol. The reaction is carried out by adding the succinimidochloroformate dissolved in an organic solvent to an organic solution of the 4-pyridylcarbinol. The reaction is conducted in a suitable solvent, such as methylene chloride, chloroform, ethyl acetate, and the like. The reaction is generally run at a low temperature, preferably between −20° to 0°C. The 4-pyridylcarbinol is added at a slow rate with stirring in order to prevent the temperature of the reaction from going above 0°C. The amount of succinimidochloroformate employed in this reaction should be slightly more than an equimolar amount of 4-pyridylcarbinol used; preferably from 1 to 10% molar excess of succinimidochloroformate is employed. After the addition of the pyridylcarbinol is completed, a tertiary organic amine, for example N-methylmorpholine, triethylamine or pyridine, is added at 0°C. The reaction is allowed to stir at a temperature of from 0° to 5°C. and then extracted successively with an acid, for example sulfuric acid, an aqueous base, for example sodium bicarbonate, and then water. The pyridyl-4-methylsuccinimide carbonate is separated and purified by methods known in the art.

The metal complex of lysine employed in this process is prepared by reacting one mole equivalent of lysine with approximately two mole equivalents of a metal salt in an aqueous medium. The metal salt is selected from the group consisting of copper, cobalt, nickel, aluminum, and the like. The lysine metal complex is obtained by mixing the reagents in an aqueous medium and can be used in the next step of the process without further separation or purification.

The preparation of N-$\epsilon$-pyridyl-4-methyloxycarbonyl lysine is accomplished by reacting a metal complex of lysine with pyridyl-4-methylsuccinimidocarbonate in an aqueous medium. The reaction is carried out under basic conditions, for example at a pH of from 7 to 12 and preferably at a pH of 10. The pH of the reaction medium is adjusted to pH 10 by addition of an aqueous base, for example 50% sodium hydroxide. The pyridyl-4-methylsuccinimidocarbonate is slowly added while the pH is maintained at 9.5 by addition of base. The addition is made at a temperature of from 0°–40°C. and preferably at 20°C. When the consumption of base has ceased, the pH is adjusted to 7.5 by addition of an acid, for example acetic acid, to precipitate the metal complex of pyridyl-4-methyloxycarbonyllysine which can be separated by filtration.

The free pyridyl-4-methyloxycarbonyllysine can be obtained by treating the metal salt with gaseous hydrogen sulfide in water or in aqueous acid, for example 10% acetic acid. The product can be recovered from the reaction mixture by methods known in the art, for example by evaporation of the solvent and crystallization.

Epsilon-pyridyl-4-methyloxycarbonyl-$\alpha$-protected lysine compounds can be prepared by reacting an $\alpha$-protected lysine with pyridyl-4-methylsuccinimidocarbonate under basic conditions, for example, pH 7 to 12 and preferably at pH 9.5. An equimolar amount of pyridyl-4-methyloxycarbonylsuccinimidocarbonate is slowly added to a basic aqueous solution of the $\alpha$-protected lysine compound at a temperature of from 0°–35°C. The pH of the reaction is maintained by addition of aqueous base, for example, aqueous sodium hydroxide. After consumption of base ceases, the reaction mixture is extracted with an organic solvent, for example, ethyl acetate, chloroform, methylene chloride, and the like. The pH of the solution is adjusted to 4.2 by addition of an acid, for example sulfuric acid, and the acidified solution extracted again with the same solvent as above. The organic extracts obtained from the acidified reaction mixture are combined, dried, and evaporated to dryness to afford the $\epsilon$-pyridyl-4-methyloxycarbonyl-$\alpha$-protected-lysine compound. Purification of the compounds can be accomplished by conventional techniques, such as recrystallization and chromatography. Alpha substituted lysine compounds which can be employed in the above process include benzyloxycarbonyllysine, p-nitrobenzyloxycarbonyllysine, p-bromobenzyloxycarbonyllysine, p-methoxybenzyloxycarbonyllysine, t-butyloxycarbonyllysine, o-nitrophenylsulfenyllysine, 2-(p-diphenyl)-isopropyloxycarbonyllysine, and the like.

The pyridyl-4-methyloxycarbonyl blocking group can be completely removed from lysine or a peptide containing a lysine residue by reaction with zinc dust in an aqueous acidic medium. The deblocking reaction is carried out by dissolving the N-$\epsilon$-pyridyl-4-methyloxycarbonyllysine compound in 50% aqueous acetic acid, and then adding the zinc dust to the solution in one portion with high speed stirring. The reaction is conveniently carried out at room temperature, although temperatures other than room temperature may also be employed. The time the reaction is allowed to stir depends on the nature of the lysine containing compound or peptide and can vary from 1 to 3 hours. The amount of zinc dust employed in the deblocking reaction can vary from 10 to 200 parts per part of pyridyl-4-methyloxycarbonyllysine compound. Complete removal of the blocking group is determined by thin layer chromatography. The deblocked peptide can be isolated by methods well known in the art, for example by gel filtration.

For preparing peptides according to the present invention, the condensation methods usual in peptide chemistry may be used, such as the carbodiimide or the azide method, or, for example, the method of mixed anhydrides or of activated esters. The peptides are built up from amino acids by condensing members selected from the group consisting of naturally occurring $\alpha$-amino acids, peptides built up from said amino acids, and derivatives thereof, and wherein at least one component of said members is lysine. More particularly, the claimed improvement comprises protecting the epsilon-amino functionality of the lysine radical with the pyridyl-4-methyloxycarbonyl group.

The term "naturally occurring amino acids" used herein is to be understood as referring to all naturally occurring amino acids in their L- or D- form, for example, alanine, arginine, aspartic acid, cysteine, cystine, glutamic acid, glycine, histidine, hydroxylysine, hydroxyproline, isoleucine, leucine, methionine, ornithine, phenylalanine, proline, serine, threonine, tyrosine, and valine.

An example of the use of the process of this invention in peptide synthesis is the preparation of the nonapeptide T27 phenylalanyl-seryl-tryptophanyl-glycyl-alanyl-glutamyl-glycyl-glutaminyl-lysine (hereinafter designated Phe-Ser-Trp-Gly-Ala-Glu-Gly-Gln-Lys) which exhibits a high degree of encephalitogenic activity. Experimental allergic encephalomyelitis (EAE) is an experimentally produced inflammatory and demyelinating disease of the central nervous system, and a study of the encephalitogenic activity of peptide T27 provides a useful model for the study of autoimmune disease. The T27 peptide can be prepared by block synthesis, wherein two peptide segments of the nonapeptide are individually synthesized and these segments are then coupled in proper sequence to form the desired peptide product. The two peptide segments are the tetrapeptide: glutamyl-glycyl-glutaminyl-(N-$\epsilon$-pyridyl-4-methyloxycarbonyl)lysine and the pentapeptide: t-butyloxycarbonylphenylalanyl-seryl-tryptophanyl-glycyl-alanine hydrazide. The lysine containing tetrapeptide is prepared in a stepwise coupling procedure by reacting N-$\epsilon$-pyridyl-4-methyloxycarbonyllysine sequentially with N-carboxy-glutamine anhydride, N-thiocarboxy anhydride of glycine and N-carboxy glutamic anhydride according to the methods known in the art. The reaction is conveniently carried out by vigorously agitating the reactants together in aqueous solution at 0°C. at a pH 10.2. The N-carboxyanhydrides of glutamine and glutamic acid and the N-thiocarboxy anhydride of glycine, prepared by methods known in the art, are added generally all at once or over a period of 15–30 seconds. Alkali, for example potassium hydroxide, is added as required to maintain the pH. The reaction of the N-thiocarboxy anhydride of glycine is carried out at a pH of 8.85. The reactions are generally completed within less than 5 minutes as judged by the cessation of base requirements. When the reaction is completed, the pH is adjusted to 3 by addition of a mineral acid, for example hydrochloric acid and the system is flushed with nitrogen to remove carbon dioxide. The tetrapeptide is isolated by freeze-drying the reaction product and purified by gel filtration, chromatography and electrophoresis.

The pentapeptide segment is prepared by the Merrifield solid phase procedure starting with t-Boc-alanine. In this procedure, the carboxyl end of alanine (and of the polypeptide product in the following steps), is bound covalently to an insoluble polymeric resin support, as for example as the carboxylic ester of the resin-bonded benzyl alcohol present in hydroxymethylsubstituted polystyrene-divinylbenzene resin. The t-butyloxycarbonyl protecting group is selectively removed by treatment of the protected aminoacyl resin with anhydrous hydrogen chloride in an organic solvent, for example dioxane. The aminoacyl resin hydrochloride which results from this treatment is then treated with a solution of triethylamine in chloroform to neutralize the hydrochloride and liberate the free amine group in a condition ready for coupling with the next amino acid. The t-butyoxycarbonyl derivative of the next amino acid desired in the peptide chain is then added, along with dicyclohexylcarbodiimide as the coupling agent. The t-butyloxycarbonyl derivatives of the following amino acids — glycine, tryptophane, serine, and phenylalanine — are added sequentially. Cleavage of the pentapeptide from the resin by treatment with hydrazine in dimethylformamide produces the pentapeptide hydrazide.

The pentapeptide azide is prepared by treating the t-Boc-Phe-Ser-Trp-Gly-Ala hydrazide in dimethylformamide with isoamylnitrite in the presence of hydrochloric acid. The reaction is run between −25° to −35°C. The azide coupling reaction is carried out by adding dropwise the tetrapeptide -Glu-Gly-Gln-($\epsilon$-i-Noc)-Lys- dissolved in dimethylformamide to the above azide solution at a pH of 5 at −10°C. The pH of the reaction mixture is adjusted to 7.2 by addition of diisopropylethylamine and the reaction is stirred at −10°C. for 20 hours to afford a clear thick gel which produces a precipitate on addition of ether. The solid is separated and washed with ether, methanol-water, and water. The product is obtained by freeze-drying the water washes and drying the residual solid in vacuo.

The tert-butyloxycarbonyl blocking group is removed from the nonapeptide by treatment with trifluoroacetic acid containing mercaptoethanol as a cation scavenger to protect the Trp nucleus. The reaction is run at 25°C. for approximately 5 minutes and the nonapeptide precipitates on addition of ether and petroleum ether. The peptide is isolated by removing the solvents and purified by chromatography. Removal of pyridyl-4-methyloxycarbonyl blocking group from the nonapeptide is accomplished by treating the peptide with zinc dust in aqueous acetic acid. The reaction is carried out at 25°C. for 1 hour. The zinc is removed from the reaction by centrifugation and the nonapeptide is purified by chromatography.

The following examples illustrate the invention, but they are not intended to limit it thereto. The abbreviated designations, which are used herein for the amino acid components, their derivatives and certain preferred protecting groups employed in this invention are as follows:

| Amino Acid | Abbreviated Designation |
| --- | --- |
| Alanine | Ala |
| Glutamic acid | Glu |
| Glutamine | Gln |
| Glycine | Gly |
| Lysine | Lys |
| Phenylalanine | Phe |
| Serine | Ser |
| Tryptophan | Trp |

| Protecting Groups | Abbreviated Designation |
| --- | --- |
| Tertiary-butyloxy-carbonyl | t-Boc |
| Pyridyl-4-methyloxy-carbonyl | i-Noc |
| Benzyl ether | OBz |
| Benzyl ester | Bz |

EXAMPLE I

A. Preparation of Epsilon-Pyridyl-4-Methyloxycarbonyllysine

1. Pyridyl-4-Methyl-succinimidocarbonate

4-Pyridylcarbinol (6.54 g., 0.06 mole) is dried by distilling off two 75 ml. portions of benzene and is dissolved in 45 ml. of methylene chloride. The solution is cooled to 0° and a solution of succinimidochloroformate (11.75 g., 0.065 mole) prepared according to the procedure described in D. Stevenson and G. T. Young, J. Chem. Soc. (c) 2389 (1969), in 60 ml. of methylene chloride is added dropwise with stirring at a rate slow enough to prevent heating above 0°C. When the addition is complete a solution of N-methylmorpholine (5.88 g., 0.058 mole) is 8 ml. of methylene chloride is added over a period of about 2 minutes at 0° with stirring. After stirring for 15 minutes at 0°–5° the solution is rapidly extracted with 150 ml. portions of 0.1N sulfuric acid, saturated sodium bicarbonate, and water. The aqueous phases are extracted with 40 ml. of methylene chloride and the combined extracts are dried over sodium sulfate. The methylene chloride solution is evaporated in vacuo, flushed with ether and triturated with ether. Filtration gave 10.4 g. of crude pyridyl-4-methyl-succinimidocarbonate. This material is dissolved in a minimum of ethyl acetate and the solution filtered. Hexane is added to the cloud point and the solution is again filtered. The procedure is carried out 4 times. After the final filtration, the solution is a light yellow color. On seeding, the pyridyl-4-methylsuccinimidocarbonate crystallizes slowly overnight: i.r. shows C=O at 4.59, 5.59, and 7.75$\mu$7.75$\mu$, m.p. 92°–94°.

2. $\epsilon$-Pyridyl-4-Methyloxycarbonyllysine

A solution of 1.82 g. (.01 mole) lysine hydrochloride in 10 ml. of water is mixed with a solution of 0.935 g. (0.005 mole) $CuCl_2 \cdot 2H_2O$ in 10 ml. of water and an additional 10 ml. of water is added. The solution is adjusted to pH 10 with 50% sodium hydroxide. Pyridyl-4-methylsuccinimidocarbonate (2.50 g., .01 mole) is added slowly with stirring and the pH maintained at 9.5 by the addition of 50% sodium hydroxide. When base consumption ceases, the pH is adjusted to 7.5 with acetic acid and the precipitated copper complex of pyridyl-4-methyloxycarbonyllysine is isolated by filtration. This precipitate is suspended in 100 ml. of 10% acetic acid and hydrogen sulfide added to precipitate Cu(II). The solution is filtered through celite and is evaporated to dryness. The resulting oil is crystallized from water-ethanol to afford $\epsilon$-N-pyridyl-4-methyloxycarbonyllysine m.p. 240°–242°C.

Removal of the blocking group from $\epsilon$-pyridyl-4-methyloxycarbonyllysine is accomplished in the following manner.

10 Mg. of N-$\epsilon$-pyridyl-4-methyloxycarbonyllysine is dissolved in 1 ml. of 50% aqueous acetic acid and 100 mg. of zinc dust is added. After stirring for 1.5 hours at 25°C., the reaction mixture is analyzed by thin layer chromatography and complete conversion to lysine is observed.

EXAMPLE II

N-$\alpha$-t-Butyloxycarbonyl-n-$\epsilon$-Pyridyl-4-Methyloxycarbonyllysine $\alpha$-Butyloxycarbonyllysine acetate (0.918 g., 0.003 mole) is dissolved in 30 ml. of water and the pH adjusted to 9.5 with N sodium hydroxide. Pyridyl-4-methylsuccinimidocarbonate (0.750 g., .003 mole) is added slowly and the pH held at 9.5 by the addition of N sodium hydroxide. When base consumption ceases, the solution is extracted 3 times with 75 ml. portions of ethyl acetate, the pH is adjusted to 4.2 by the addition of 2.5 N sulfuric acid. The solution is extracted 4 times with 75 ml. portions of ethyl acetate. The organic extracts at pH 4.2 are combined, dried over sodium sulfate, and evaporated to dryness. Crystallization from ethyl acetate-ethyl ether gives 0.76 g. of N-$\alpha$-t-butyloxycarbonyl-N-$\epsilon$-pyridyl-4-methyloxycarbonyllysine, m.p. 69.5°–71.5°C.; i.r. shows N-H 3.03, C=O 5.85, 5.96$\mu$.

The removal of the blocking group from N-$\alpha$-tert-butyloxycarbonyl-N-$\epsilon$-pyridyl-4-methyloxycarbonyllysine is accomplished in the following manner.

10 Mg. of N-$\alpha$-tert-butyloxycarbonyl-N-$\epsilon$-pyridyl-4-methyloxycarbonyllysine is dissolved in 1 ml. of 50% aqueous acetic acid and 100 mg. of zinc dust is added. After stirring for 4 hours at 25°C., analysis by thin layer chromatography indicates complete conversion to N-$\alpha$-tert-butyloxycarbonyllysine.

When N-$\alpha$-tert-butyloxycarbonyl-N-$\epsilon$-pyridyl-3-methyloxycarbonyllysine, prepared by the method described above, is employed in the deblocking process in place of N-$\alpha$-tert-butyloxycarbonyl-N-$\epsilon$-pyridyl-4-methyloxycarbonyllysine and the reaction is stirred for 24 hours, only about 5% of the $\epsilon$-pyridyl-3-methyloxycarbonyl blocking group is removed as ahown by thin layer chromatography.

EXAMPLE III

Preparation of Phenylalanyl-Seryl-Tryptophanyl-Glycyl-Alanyl-Glutamyl-Glycyl-Glutaminyl-Lysine A. Preparation of Glutamyl-Glycyl-Glutaminyl-(N-$\epsilon$-pyridyl-4-methyloxycarbonyl) Lysine The N-$\epsilon$-pyridyl-4-methyloxcarbonyllysine, 421.7 mg. (1.5 mmoles) and 20 ml. of potassium borate buffer (pH 10.2) are placed in a Waring Blender at 0°C. To this is added 0.276 mg. (1.61 mmoles; 7% molar excess) of crystalline N-carboxy anhydride of glutamine in one portion with rapid stirring. The pH is maintained at 10.2 by addition of 0.55 ml. of 5N potassium hydroxide. The reaction is complete in about 2 minutes and the pH is adjusted to 3 by addition of concentrated hydrochloric acid; the system is flushed with nitrogen to remove carbon dioxide. The pH of the reaction mixture is then raised to 8.85 by addition of 5N potassium hydroxide and 197 mg. (1.675 mmoles; 5% molar excess) of N-thiocarboxy anhydride of glycine is added in one portion. The addition of 0.47 ml. of 5N potassium hydroxide requires 1.5 minutes and the reaction is stirred for 5 minutes. The pH is adjusted to 3 by addition of concentrated hydrochloric acid and the system is flushed with nitrogen to remove carbon oxysulfide. The pH of the reaction mixture is raised to 10.1 by addition of 5N potassium hydroxide and 300 mg. (1.74 mmoles, 3% molar excess) of solid N-carboxy glutamic acid anhydride is added in one portion. The pH of the reaction is maintained by addition of 0.65 ml. of 5N potassium hydroxide and the reaction is stirred at pH 10.1 for 1.75 minutes. The pH is adjusted to 3 by addition of concentrated hydrochloric acid and the reaction product freeze dried to afford 7.09 g. This crude freeze dried material is extracted with methanol (once with 100 ml. and 4 times with 50 ml.) and the extracts concentrated in vacuo to afford 1.27 g. of Glu-Gly-Gln-($\epsilon$-1-Noc)-Lys. The extracted tetrapeptide is purified in the following manner: (a) chromatographed twice on Sephadex G-50 fine in 50% acetic acid; (b) chromatographed on Silica gel column, using chloroform:methanol:water (60:40:10:) as eluent; and (c) preparative electrophoresis in pyridineacetate buffer at pH 6.4.

B. Preparation of t-Butyloxycarbonyl-Phenylalanyl-Seryl-Tryptophanyl-Glycyl-Alanine Hydrazide The pentapeptide hydrazide is prepared by solid phase peptide synthesis in the following manner:

One gram (.77 mmoles) t-Boc-Ala-Resin is suspended is 30 ml. of methylene chloride at room temperature. The amino acid resin is treated as follows: (a) wash 3 times with 15 ml. of dixoane; (b) remove the terminal t-Boc group by reacting 15 ml. of 4N hydrochloric acid in dioxane; (c) wash the deblocked material 3 times with 15 ml. dioxane; (d) wash 3 times with 15 ml. of chloroform; (e) neutralize the material with 15 ml. of a mixture of triethylamine in chloroform (1:9); (f) wash the neutralized material 3 times with 15 ml. chloroform; (g) wash 3 times with 15 ml. methylene chloride; (h) add 338 mg. of t-Boc-Gly in methylene chloride; (i) couple by adding 397.6 mg. of NN-dicyclohexylcarbodiimide in methylene chloride and allowing the reaction to run for two hours; (j) wash the t-Boc-Gly-Ala-Resin 3 times with 15 ml. of methylene chloride. By repeating these operations with the following amino derivatives, t-Boc-Trp (586 mg.), t-Boc-Ser (396 mg.), t-Boc-Phe (510 mg.), the pentapeptide resin, t-Boc-Phe-Ser-Trp-Gly-Ala-Resin, is prepared. After coupling of t-Boc-Trp, the deblocking with hydrochloric acid is carried out in the presence of mercaptolethanol to avoid alkylation of Trp. The peptide-Resin is washed 3 times with 15 ml. ethanol, 3 times with 15 ml. acetic acid, 3 times with 15 ml. ethanol, and 5 times with 15 ml. methylene chloride and dried in vacuo to afford 1.3 gm. of t-Boc-Phe-Ser-Trp-Gly-Ala-Resin.

1.3 G. of t-Boc-Phe-Ser-Trp-Gly-Ala-Resin is treated with 12 ml. of a 1:1 mixture of hydrazine in dimethylformamide for 2 hours. The resin is collected by filtration and washed two times with 10 ml. of dimethylformamide. The dimethylformamide washes and filtrate are combined and the solvents are removed in vacuo to produce an oily residue. The product crystallizes on standing. The solid is washed five times with 20 ml. of ethyl acetate and dried in vacuo to remove traces of ethylacetate. The dried solid is washed with 15 ml. portions of water until all hydrazine and dimethylformamide impurities are removed. 378.1 Mg. of t-Boc-Phe-Ser-Trp-Gly-Ala-hydrazide is obtained.

C. Azide coupling of Peptide Fragments A and B t-Boc-Phe-Ser-Trp-Gly-Ala-NHNH$_2$ (144.5 mg., 0.210 mm) is suspended in 1.5 ml. of dimethylformamide and the mixture is cooled to −40°. When 0.150 ml. of HCl in tetrahydrofuran is added, a clear solution is obtained, having a pH of 1. The solution is maintained at −25° to −30° and a total of 33λ of isoamylnitrite, 116% of theory, is added in portions during an 18 min. period until a faintly positive starch-iodide test is constant for 12 minutes. Tlc in cloroform-methanol-water (85:15:1.5) on silica indicates that all of the hydrazide has been converted into Tollens-negative material. An essentially single spot azide is detected by hypochlorite-starch-iodide spray.

Glu-Gly-Gln-(ε-i-Noc)-Lys (150 mg., 0.252 mm., 20% excess) is dissolved in 0.8 ml. of dimethylformamide and added to the azide solution which has been adjusted to pH 5 with 0.15 ml. of diisopropylethylamine. The tube containing the nucleophile is washed out with 2 × 0.2 ml. and 1 × 0.1 ml. of dimethylformamide. The reaction mixture is adjusted to pH 7.2 by addition of 100λ of diisopropylethylamine. A total of 8 equivalents of amine is used after 10 minutes at −10°, tlc in chloroform-methanol-water (60:40:10) and chloroform-methanol-water-ammonia (60:30:4:6) shows that the reaction is almost complete, using Ehrlich, ninhydrin, and hypochlorite spray for detection of products. After the reaction mixture has been stirred magnetically at −10° for 20 hours, it is a clear thick gel and addition of 20 ml. of ether gives a precipitate.

The mixture is kept at 0° until a clear supernatant liquid is obtained. The precipitate is removed by centrifugation and washed with 10 ml. of ether, 2 × 10% methanol-ether, and 2 × 10 ml. of water. By freeze-drying the water washes, 106 mg. of product is obtained. The residual solid after being dried in vacuo weighs 195 mg.

Gel filtration is used to purify the water washes. The 106 mg. is dissolved in 4 ml. of 50% acetic acid and charged on Sephadex G-50, fine, column.

Solvents are removed in vacuo and the residue is freeze-dried to t-Boc-Phe-Ser-Trp-Gly-Ala-Glu-Gly-Gln-(ε-i-Noc)-Lys.

Amino acid analysis after 20 hr. acid hydrolysis: Phe$_{1.01}$ Ser$_{1.00}$ Trp$_{0.75}$ Gly$_{2.00}$ Ala$_{1.00}$ Glu$_{1.99}$ Lys$_{1.00}$. MW 1475 found.

Phe-Ser-Trp-Gly-Ala-Glu-Gly-Gln-(ε-i-Noc)-Lys

A 94 mg. sample of the washed solid above is mixed with 1.5 ml. of trifluoroacetic acid, containing 1% mercaptoethanol as a cation scavenger to protect the Trp nucleus. In 3 min. at 25° the solid dissolves completely, and the solution is kept an additional 2.5 min. at 25°. The deblocked peptide is precipitated with 10 ml. of cold ether and 10 ml. of cold petroleum ether and washed with 2 × 5 ml. of ether. After being dried in vacuo, the crude peptide weighs 109 mg.

For purification, the product is dissolved in 6 ml. of 50% acetic acid with cooling in an ice bath. It is slowly soluble, requiring 30 min. for complete dissolution. The solution is charged into a 2.5 × 100 cm. column of Sephadex G-50, fine, and washed out with 2 × 1 ml. of 50% acetic acid.

6.2 Ml. fractions are collected every 20 min. Fractions 64-72 are combined, concentrated in vacuo and freeze-dried, giving 78.50 mg. of Phe-Ser-Trp-Gly-Ala-Glu-Gly-Gln-(ε-i-Noc)-Lys.

Amino acid analysis after 20 hr. acid hydrolysis: Phe$_{0.99}$ Ser$_{1.00}$ Trp$_{0.77}$ Gly$_{2.00}$ Ala$_{1.00}$ Glu$_{2.02}$ Lys$_{0.99}$.

Phe-Ser-Trp-Gly-Ala-Glu-Gly-Gln-Lys : Zn-acetic acid cleavage of N-ε-pyridyl-4-methyloxycarbonyl blocking group — a mixture of 5.94 mg. of Phe-Ser-Trp-Gly-Ala-Glu-Gly-Gln-(ε-i-Noc)-Lys in 0.7 ml. of 50% acetic acid and 130 mg. of zinc dust is stirred at 25° for 1 hr. The zinc is removed by centrifugation. One-Half of the reaction is charged on a 2.5 cm × 100 cm column of Sephadex G-50 (fine). The flow rate is 8.5 ml/20 min., separation is followed by a U.V. monitor at 280 nm, and fractions 46–49 are combined, concentrated in vacuo and freeze-dried: 1.43 mg. of Phe-Ser-Trp-Gly-Ala-Glu-Gly-Gln-Lys is obtained. It shows a single zone by tlc in chloroform-methanol-water (40:47:13), by hypochlorite, Ehrlich, and ninhydrin reagents.

EXAMPLE IV

Preparation of Glutamyl-Glutamyl-Lysyl-Seryl-Alanine t-Boc-Ala-Resin (6.5 g., 5 mm.) is treated in the following manner: (a) wash the amino acid resin 3 times with 45 ml. of methylene chloride; (b) wash 3 times with 45 ml. ethanol; (c) wash 3 times with 45 ml. of acetic acid; (d) remove the terminal t-Boc protecting group by treating the amino acid resin material with anhydrous hydrogen chloride in acetic acid for 30 minutes; (e) wash the deblocked Ala-Resin 3 times with acetic acid; (f) wash 3 times with ethanol; (g) wash 3 times with methylene chloride; (h) neutralize the Ala-Resin by treating it with 40 ml. of a solution of triethylamine in methylene chloride (1:9) for 10 minutes; (i) wash 5 times with methylene chloride; (j) add 3.7 g. (12.5 mm.) of t-Boc-O-Bz-Serine in 30 ml. methylene chloride and stir for 10 minutes; (k) couple by adding 12.5 mml. of N,N'-dicyclohexylcarbodiimide in methylene chloride to the reaction and allow it to stir for 2 hours; (m) wash the t-Boc-O-Bz-Ser-Ala-Resin 3 times with methylene chloride and 3 times with ethanol. By repeating the above operations and employing the following amino acids, α-Boc -ε-i-Noc-lysine 4.9 g. (12.5 mm), α-Boc-γ-Bz-glutamic acid 4.3 g. (12.5 mm), and α-Boc-γ-Bz-glutamic acid 4.3 g. (12.5 mm), 10.9 g. of the pentapeptide -continued

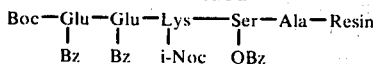

is obtained.

Removal of the pentapeptide from the resin is accomplished by cooling a mixture of 2.2 g. (1 mm.) of the above peptide-Resin product in 3 ml. of veratrole to 0.5°C. and adding 10 ml. of trifluoroacetic acid. Then 10 ml. of hydrogen fluoride is condensed into the reaction mixture using an acetone-dry ice bath. The cooling bath is removed and the reaction is stirred at room temperature for 1 hour. The hydrogen fluoride and trifluoroacetic acid are removed by passing a stream of nitrogen through the reacton with stirring. The residue is treated 2 times with 25 ml. of 5% aqueous acetic acid. The resin is removed by filtration and washed 3 times with 15 ml. of ethyl ether. The aqueous filtrate is washed 2 times with 15 ml. of ether. The aqueous portion is freeze-dried twice to afford 700 mg. of Glu-Glu-(ε-i-Noc)-Lys-Ser-Ala.

The epsilon blocking group of lysine is removed by mixing 10 mg. of Glu-Glu-(ε-i-Noc)-Lys-Ser-Ala and 100 mg. of zinc dust in 1 ml. of 50% aqueous acetic acid at room temperature for 1½ hours. Tlc indicated complete removal of i-Noc blocking group.

The t-Boc-Ala-Resin starting material for the solid phase peptide synthesis in the above examples is prepared in the following manner: 50 g. (92.5 meq. Cl) chloromethylated polystyrene resin with 1% crosslinking and 1.85 meq. Cl/gm. (Bio-Beads S-X1 200–400 Mesh Chloromethylated available from Bio-Rad Laboratories) and 17.5 g. (92.5 meq.) of t-Boc-Ala is added to 350 ml. peroxide free tetrahydrofuran. The reaction is stirred under nitrogen and 8.4 gm. (83.3 meq.) triethylamine is added in 50 ml. of tetrahydrofuran. The reaction is heated at reflux in an oil bath for 65 hours. The reaction is cooled at room temperature and filtered. The solid material is washed 2 × 250 ml. ethanol, 2 × 250 ml. water, 2 × 250 ml. methanol, and 2 × 500 ml. methylene chloride and dried in vacuo at room temperature to yield 55.7 gm. t-Boc-Ala-Resin which contains 0.770 meq. of t-Boc-Ala/gm. of solid.

What is claimed is:

1. The process for the preparation of ε-pyridyl-4-methyloxycarbonyllysine which comprises reacting a copper complex of lysine with pyridyl-4-methyl-succinimide carbonate at a pH of 7–12.

* * * * *